United States Patent [19]

Bock et al.

[11] Patent Number: 4,517,294

[45] Date of Patent: May 14, 1985

[54] HUMAN ANTITHROMBIN III

[75] Inventors: Susan C. Bock, Palo Alto; Richard M. Lawn, San Francisco, both of Calif.

[73] Assignee: Genentech, Inc., South San Francisco, Calif.

[21] Appl. No.: 403,600

[22] Filed: Jul. 30, 1982

[30] Foreign Application Priority Data

Mar. 3, 1982 [GB] United Kingdom ............... 8206262

[51] Int. Cl.³ .................... C12P 21/02; C12N 15/00; C12N 1/20; C12N 1/00; C07H 15/12

[52] U.S. Cl. .................................. 435/70; 435/172.3; 435/253; 435/317; 536/27; 935/4; 935/11; 935/21; 935/29; 935/60; 935/73

[58] Field of Search ............... 435/172, 253, 68, 70, 435/71, 317; 536/27; 935/9, 11, 60, 70, 71, 73

[56] References Cited

U.S. PATENT DOCUMENTS 4,087,415 5/1978 Bick et al. .................. 260/112 B
4,382,028 5/1983 Paget ........................ 260/112 B

FOREIGN PATENT DOCUMENTS 2354340 6/1978 France .

OTHER PUBLICATIONS

Lawn et al., Nucleic Acids Research 9(22), 6103–6114 (1981).

Helling et al., Genetic Engineering edited by Chakrabarty, CRC Press Inc., pp. 1–30 (1978).

S. Bock et al., "Nucleic Acids Research" 10(24): 8113–8125 (1982).

S. Bock et al., "P.N.A.S. USA" 79: 1032–1036 (Feb. 1982).

T. MacGillivray et al., "Chemical Abstracts" 91: 234 No. 135914d (1979).

K. Kurachi et al., "P.N.A.S. USA" 78(11): 6826–6830 (Nov. 1981).

Primary Examiner—Alvin E. Tanenholtz

[57] ABSTRACT

A DNA sequence encoding human antithrombin III, cloning vehicles and cells containing that DNA sequence.

10 Claims, 3 Drawing Figures

```
CACCAGCATCATCTCCTCCAATTCATCCAGCTACTCTGCCCATGAAGATAATAGTTTTCAGGCGGATTGCCTCAGATCACACTATCTCCACTTGCCCAGCCCTGTGGAAGATTAGCGGCC (Signal)
Met Tyr Ser Asn Val Ile Gly Thr Val Thr Ser Gly Lys Arg Lys Val Tyr Leu Leu Ser Leu Leu Leu Ile Gly Phe Trp Asp Cys Val
ATG TAT TCC AAT GTG ATA GGA ACT GTA ACC TCT GGA AAA AGG AAG GTT TAT CTT TTG TCC TTG CTG CTC ATT GGC TTC TGG GAC TGC GTG 1 (Mature)
Thr Cys|His Gly Ser Pro Val Asp Ile Cys Thr Ala Lys Pro Arg Asp Ile Pro Met Asn Pro Met Cys Ile Tyr Arg Ser Pro Glu Lys
ACC TGT|CAC GGG AGC CCT GTG GAC ATC TGC ACA GCC AAG CCG CGG GAC ATT CCC ATG AAT CCC ATG TGC ATT TAC CGC TCC CCG GAG AAG
                                                                                        50
Lys Ala Thr Glu Asp Glu Gly Ser Glu Gln Lys Ile Pro Glu Ala Thr Asn Arg Arg Val Trp Glu Leu Ser Lys Ala Asn Ser Arg Phe
AAG GCA ACT GAG GAT GAG GGC TCA GAA CAG AAG ATC CCG GAG GCC ACC AAC CGG CGT GTC TGG GAA CTG TCC AAG GCC AAT TCC CGC TTT Ala Thr Thr Phe Tyr Gln His Leu Ala Asp Ser Lys Asn Asp Asn Asp Asn Ile Phe Leu Ser Pro Leu Ser Ile Ser Thr Ala Phe Ala
GCT ACC ACT TTC TAT CAG CAC CTG GCA GAT TCC AAG AAT GAC AAT GAT AAC ATT TTC CTG TCA CCC CTG AGT ATC TCC ACG GCT TTT GCT
                                            100
Met Thr Lys Leu Gly Ala Cys Asn Asp Thr Leu Gln Gln Leu Met Glu Val Phe Lys Phe Asp Thr Ile Ser Glu Lys Thr Ser Asp Gln
ATG ACC AAG CTG GGT GCC TGT AAT GAC ACC CTC CAG CAA CTG ATG GAG GTA TTT AAG TTT GAC ACC ATA TCT GAG AAA ACA TCT GAT CAG Ile His Phe Phe Phe Ala Lys Leu Asn Cys Arg Leu Tyr Arg Lys Ala Asn Lys Ser Ser Lys Leu Val Ser Ala Asn Arg Leu Phe Gly
ATC CAC TTC TTC TTT GCC AAA CTG AAC TGC CGA CTC TAT CGA AAA GCC AAC AAA TCC TCC AAG TTA GTA TCA GCC AAT CGC CTT TTT GGA
    150
Asp Lys Ser Leu Thr Phe Asn Glu Thr Tyr Gln Asp Ile Ser Glu Leu Val Tyr Gly Ala Lys Leu Gln Pro Leu Asp Phe Lys Glu Asn
GAC AAA TCC CTT ACC TTC AAT GAG ACC TAC CAG GAC ATC AGT GAG TTG GTA TAT GGA GCC AAG CTC CAG CCC CTG GAC TTC AAG GAA AAT
                                                                                    200
Ala Glu Gln Ser Arg Ala Ala Ile Asn Lys Trp Val Ser Asn Lys Thr Glu Gly Arg Ile Thr Asp Val Ile Pro Ser Glu Ala Ile Asn
GCA GAG CAA TCC AGA GCG GCC ATC AAC AAA TGG GTG TCC AAT AAG ACC GAA GGC CGA ATC ACC GAT GTC ATT CCC TCG GAA GCC ATC AAT Glu Leu Thr Val Leu Val Leu Val Asn Thr Ile Tyr Phe Lys Gly Leu Trp Lys Ser Lys Phe Ser Pro Glu Asn Thr Arg Lys Glu Leu
GAG CTC ACT GTT CTG GTG CTG GTT AAC ACC ATT TAC TTC AAG GGC CTG TGG AAG TCA AAG TTC AGC CCT GAG AAC ACA AGG AAG GAA CTG
                                        250
Phe Tyr Lys Ala Asp Gly Glu Ser Cys Ser Ala Ser Met Met Tyr Gln Glu Gly Lys Phe Arg Tyr Arg Arg Val Ala Glu Gly Thr Gln
TTC TAC AAG GCT GAT GGA GAG TCG TGT TCA GCA TCT ATG ATG TAC CAG GAA GGC AAG TTC CGT TAT CGG CGC GTG GCT GAA GGC ACC CAG Val Leu Glu Leu Pro Phe Lys Gly Asp Asp Ile Thr Met Val Leu Ile Leu Pro Lys Pro Glu Lys Ser Leu Ala Lys Val Glu Lys Glu
GTG CTT GAG TTG CCC TTC AAA GGT GAT GAC ATC ACC ATG GTC CTC ATC TTG CCC AAG CCT GAG AAG AGC CTG GCC AAG GTG GAG AAG GAA
    300
Leu Thr Pro Glu Val Leu Gln Glu Trp Leu Asp Glu Leu Glu Glu Met Met Leu Val Val His Met Pro Arg Phe Arg Ile Glu Asp Gly
CTC ACC CCA GAG GTG CTG CAG GAG TGG CTG GAT GAA TTG GAG GAG ATG ATG CTG GTG GTT CAC ATG CCC CGC TTC CGC ATT GAG GAC GGC
                                                                            350
Phe Ser Leu Lys Glu Gln Leu Gln Asp Met Gly Leu Val Asp Leu Phe Ser Pro Glu Lys Ser Lys Leu Pro Gly Ile Val Ala Glu Gly
TTC AGT TTG AAG GAG CAG CTG CAA GAC ATG GGC CTT GTC GAT CTG TTC AGC CCT GAA AAG TCC AAA CTC CCA GGT ATT GTT GCA GAA GGC Arg Asp Asp Leu Tyr Val Ser Asp Ala Phe His Lys Ala Phe Leu Glu Val Asn Glu Glu Gly Ser Glu Ala Ala Ala Ser Thr Ala Val
CGA GAT GAC CTC TAT GTC TCA GAT GCA TTC CAT AAG GCA TTT CTT GAG GTA AAT GAA GAA GGC AGT GAA GCA GCT GCA AGT ACC GCT GTT
                                        400
Val Ile Ala Gly Arg Ser Leu Asn Pro Asn Arg Val Thr Phe Lys Ala Asn Arg Pro Phe Leu Val Phe Ile Arg Glu Val Pro Leu Asn
GTG ATT GCT GGC CGT TCG CTA AAC CCC AAC AGG GTG ACT TTC AAG GCC AAC AGG CCC TTC CTG GTT TTT ATA AGA GAA GTT CCT CTG AAC Thr Ile Ile Phe Met Gly Arg Val Ala Asn Pro Cys Val Lys End
ACT ATT ATC TTC ATG GGC AGA GTA GCC AAC CCT TGT GTT AAG TAA AAT GTT CTT ATT CTT TGC ACC TCT TCC TAT TTT TGG TTT GTG AAC
AGA AGT AAA AAT AAA TAC AAA CTA CTT CCA TCT CAC ATT PolyA
```

FIG. 2.

ic role in maintaining the fluidity of blood. Blood coagulation is mediated by a series of serine proteases. Antithrombin III is a potent inhibitor of Factors IXa, Xa (Kurachi et al., 1976)[1], XI (Damus et al., 1973), XIIa (Stead et al., 1976), and thrombin (Rosenberg et al., 1973). Thus, ATIII regulates clot formation both at the activation level and the thrombin level. The physiological importance of ATIII in preventing excessive coagulation is revealed by studies of individuals whose antithrombin levels are decreased due to heredity (Egeberg, 1965; Odegard et al., 1977; Van der Meer et al., 1973; and Sas et al., 1974) or acquired deficiency (Abildgaard et al., 1970; Mannucci et al., 1973; Fagerhol et al., 1970). Such persons are prone to spontaneous thrombosis and the associated risks of disseminated intravascular coagulation (DIC), cardiac infarction, cerebrovascular accident, pulmonary embolism, etc. Transfusion of patients suffering from severe bleeding disorders complicated by DIC with antithrombin III concentrates obtained by blood fractionation has suggested that such replacement therapy can restore normal hemostatic function (Schipper et al., 1978).

[1] Reference is made to the appended bibliography which is hereby made a part hereof, the publications and other materials there correspondingly cited in more detail being incorporated herein by reference.

Human antithrombin III is a single-chain glycoprotein synthesized by the liver and found in plasma at a concentration of approximately 20 mg/dl (Collen et al., 1977). Molecular weight determinations for antithrombin III have yielded values between 54,000 and 65,000 daltons (Rosenberg and Damus, 1973; Nordenman et al., 1977; Kurachi et al., 1976), of which some 10 percent is carbohydrate (Kurachi et al., 1976). The primary amino acid structure of human antithrombin III has been almost completely determined by Petersen et al. (1979) (who reported that this protein has approximately) 430 amino acid residues, 4 glucosamine-based oligosachride side units, and 3 disulfide bridges. However, these workers were uncertain as to the precise identity of several amino acids, and moreover, did not identify the sequence and length of an amino acid stretch in the middle of the protein due to incompletely overlapped peptides.

ATIII inactivates thrombin by forming a covalent 1:1 stoichiometric complex with the protease (Rosenberg and Damus, 1973; Owen, 1975). The anticoagulant effect of antithrombin III is enhanced by heparin, which greatly increases the rate of inhibitor-protease complex formation (Abildgaard, 1968).

It was thought possible that therapeutic administration of human antithrombin III produced by genetically engineered microorganisms would also be useful in the clinical prevention and management of thromboses. Such genetic engineering methods would provide sufficient quantities of material so as to enable its clinical testing as a demonstration of the safety and efficacy prerequisites to marketing. Therefore, the task was undertaken of cloning the gene for human antithrombin III and expressing it in a host cell.

SUMMARY OF THE INVENTION

The present invention is directed to the means and methods of producing human antithrombin III via recombinant DNA technology, including (1) the discovery and identity of the entire DNA sequence of the mature protein as well as its signal polypeptide, and the 3'- and 5'-flanking regions thereof; (2) the construction of cloning and expression vehicles comprising said DNA sequence, enabling the amplification, and thence, expression of the mature human antithrombin III protein, as well as Met, fusion, or signal N-terminus conjugates thereof; and (3) viable cell cultures, genetically altered by virtue of their harboring such vehicles and capable of producing human antithrombin III polypeptide. Further, this invention provides human antithrombin III in physical state distinct from its existence in, or isolation from, a natural environment or source, it by virtue of its method of preparation herein, being essentially free of usual endogenous proteins and other native materials or substances.

This invention is directed to the recombinant DNA production of human antithrombin III in all of its aspects, and is not to be construed as limited to any specific details described herein and embraced within the compass of this invention. For example, the term "mature" as used herein connotes human ATIII as well as methionyl as a first amino acid, present by virtue of the ATG translational codon in the expression vector construction hereof.

DESCRIPTION OF PREFERRED EMBODIMENTS

The work described herein was performed employing, inter alia, the microorganism *E. coli* K-12 strain 294 (end A, thi$^-$, hsr$^-$, $_k$hsm$^+$), as described in British Patent Application Publication No. 2055382A.

This strain has been deposited with the American Type Culture Collection, ATCC Accession No. 31446, on Oct. 28, 1978. However, various other microbial strains are useful, including known *E. coli* strains such as *E. coli* B, *E. coli* ×1776 (ATCC No. 31537, deposited July 3, 1979) and *E. coli* W3110 (F$^-$, $\zeta^-$, protrophic) (ATCC No. 27325), or other microbial strains many of which are deposited and (potentially) available from recognized microorganism depository institutions, such as the American Type Culture Collection (ATCC)—cf. the ATCC catalogue listing. See German Offenlegungsschrift No. 2644432. These other microorganisms include, for example, Bacilli such as *Bacillus subtilis* and other enterobacteriaceae among which can be mentioned as examples *Salmonella typhimurium* and *Serratia marcesans*, utilizing plasmids that can replicate and express heterologous gene sequences therein.

Expression plasmids for bacterial use, e.g., *E. coli* are commonly derived using pBR322 as vector and appropriately inseting the heterologous gene sequence together with translational start and stop signals in operable reading phase with a functional promoter, taking advantage of common or synthetically created restriction sites. The vector will carry one or more phenotypic selection characteristics genes and an origin of replication to insure amplification within the host. Again, the heterologous insert can be aligned so as to be expressed together with a fused presequence, derivable for example from the trp system genes.

The present invention may also employ various yeast strains, hosting compatible expression vectors, such as the plasmid YRp7 (see Stinchcomb et al., *Nature* 282, 39 (1979)), which is capable of selection and replication in both *E. coli* and yeast, particularly *Saccharomyces cerevisiae*. A useful strain is strain RH218 (Mioggari et al., J.

Bacteriology 134, 48 (1978)) deposited with the American Type Culture Collection without restriction (ATCC No. 44076).

To express a heterologous gene such as the cDNA for human antithrombin III in yeast, it is necessary to construct a plasmid vector containing four components. The first component is the part which allows for transformation of both *E. coli* and yeast and thus must contain a selectable gene from each organism. This can be the gene for ampicillin resistance from *E. coli* and the gene TRP1 from yeast. This component also requires an origin of replication from both organisms to be maintained as a plasmid DNA in both organisms. This can be the *E. coli* origin from pBR322 and the ars 1 origin from chromosome III of yeast or the origin of replication from 2μ circle DNA.

The second component of the plasmid is a 5'-flanking sequence from a highly expressed yeast gene to promote transcription of a downstream-placed structural gene. The 5'-flanking sequence can be that from the yeast 3-phosphoglycerate kinase (PGK) gene. The fragment is constructed in such a way so as to remove the ATG of the PGK structural sequence, replaced with a sequence containing alternative restriction sites, such as XbaI and EcoRI restriction sites, for convenient attachment of this 5'-flanking sequence to the structural gene.

The third component of the system is a structural gene constructed in such a manner that it contains both an ATG translational start and translational stop signals.

The fourth component is a yeast DNA sequence containing the 3'-flanking sequence of a yeast gene, which contains the proper signals for transcription termination and polyadenylation.

For example, plasmids directing the production of methionyl-ATIII and pre ATIII in yeast can be constructed by respectively inserting gene fragments for the mature protein and mature protein plus signal peptide into the EcoRI site of 8.6 kbp expression plasmid YEp1PT. (Hitzeman et al, *Proc. of Berkeley Workshop on Recent Advances in Yeast Molecular Biology*, 20–22 May '82, University of California, Berkeley.) The YEp1PT vector contains a PbR322 origin to allow bacterial replication as well as a yeast 2μ origin. YEp1PT also carriers an ampicillin resistance marker as a selectable trait in *E. coli* and the yeast TRP1 gene which is used to maintain the plasmid in tryptophan auxotrophic yeast strains. A unique Eco RI cloning site is immediately downstream of a 1.6 kb yeast DNA fragment carrying the efficient promoter for the 3-phosphoglycerate kinase (PGK) gene. The ATIII structural gene fragments generated by complete EcoRI and partial PstI digestion of pATIII-E7 or pATIII-J4 (see infra.) can be inserted into the YEp1PT EcoRI site adjacent to the PGK promoter. A 247 bp PstI-EcoRI DNA fragment derived from yeast 2μ circle DNA is useful to convert the PstI sites at the 3' ends of the ATIII inserts into EcoRi ends; this convertor fragment also provides 2μ terminator function.

Similarly, the present inventions can employ various cell culture systems with appropriate vectors. One useful host for the production of heterologous protein is the COS-7 line of monkey kidney fibroblasts (Gluzman, *Cell* 23, 175 (1981)). However, the present invention could be practiced in any cell line that is capable of replication and expression of a compatible vector, e.g., WI38, BHK, 3T3, CHO, VERO, and HeLa cell lines. Additionally, what is required of the expression vector is an origin of replication and a promoter located in front of the gene to be expressed, along with any necessary ribosome binding sites, RNA splice sites, polyadenylation site, and transcriptional terminator sequences. It will be understood that this invention, although described herein in terms of a preferred embodiment, should not be construed as limited to these sequences. For example, the origin of replication of SV40 and other viral (e.g., Polyoma, Adeno, VSV, BPV, and so forth) vectors could be used, as well as cellular origins of DNA replication which could function in a nonintegrated state.

The strategy for the synthesis of heterologous peptide in mammalian cell culture relies on the development of a vector capable of expression of a foreign gene under the control of a transcriptional unit. The replication of this vector in tissue culture can be accomplished by providing a DNA replication origin (such as from SV40 virus), and providing helper function (T antigen) by the introduction of the vector into a cell line endogenously expressing this antigen (Lusky et al., *Nature* 293, 79 (1981)). A promoter of SV40 virus precedes the structural gene and ensures the transcription of the gene. Alternatively, the expressed gene can be incorporated into the cellular genome via procedures known per se so as to ensure stable transmission of the gene.

A useful vector to obtain expression consists of pBR322 sequences which provides a selectable marker for selection in *E. coli* (ampicillin resistance) as well as an *E. coli* origin of DNA replication. These sequences are derivable from the plasmid pML-1 (Lusky et al., *Nature* 293, 79 (1981)). The SV40 origin is derivable from a 342 base pair PvuII-HindIII fragment encompassing this region (Fiers et al, *Nature* 273, 113 (1978)) (both ends being convertable to EcoRI ends). These sequences, in addition to comprising the viral origin of DNA replication, encode the promoter for both the early and late transcriptional unit. The orientation of the SV40 origin region is such that the promoter for the early transcriptional unit is positioned proximal to the gene encoding human antithrombin III.

BRIEF DESCRIPTION OF THE DRAWINGS

FIG. 2 shows the nucleotide and amino acid sequence of human antithrombin III. The nucleotide sequence of the human ATIII mRNA was determined from DNA sequence analysis of the cDNA clones pA62 and pA68. Predicted amino acids of the signal and mature ATIII polypetide are shown above the DNA sequence and are numbered from the first residue of the mature protein. The nucleotide sequence shown does not extend to the true 5' terminus of ATIII mRNA.

DETAILED DESCRIPTION

Methods

Figure 1:
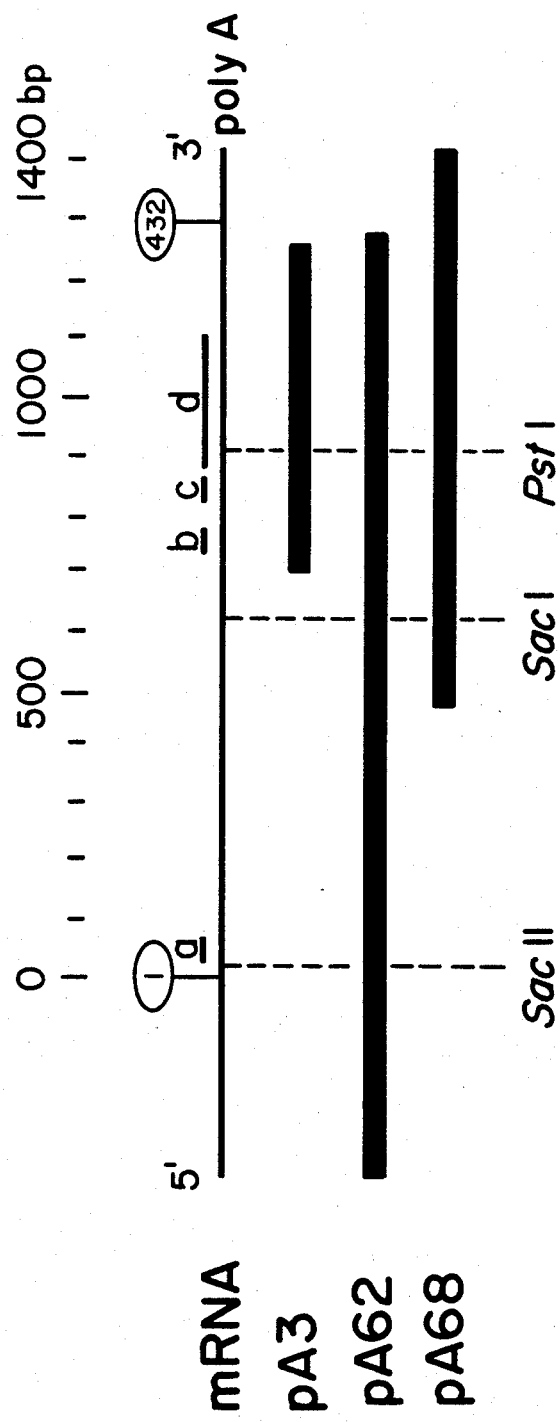
FIG. 1 depicts antithrombin III mRNA and cDNA clones. The top line represents the mRNA coding for human antithrombin III. DNAs employed as primers and hybridization probes are indicated by bars and the letters a–d above the mRNA. (a) pool of eight N-14 mers, (b) pool of eight i-16 mers, (c) i-14mer (d) 230 bp Dde I fragment. The initial and final amino acid codons of the mature ATIII polypeptide are indicated by the circled 1 and 432 respectively. Key restriction endonuclease sites are shown by vertical lines. An approximate size scale in nucleotides is included.

RNA preparation.

Human liver messenger RNA was prepared by the guanidinium thiocyanate method (Ullrich et al., 1977) followed by oligo dT cellulose chromatography (poly-(A)+RNA), or by phenol extraction of polysomes isolated in the presence of the potent ribonuclease inhibitor, hydroxystilbamidine isethionate (Lizardi, 1980) (polysomal RNA). To obtain approximately 3 mg of polysomal RNA, 5 g of liver were homogenized in 10 mM NaCl, 1.5 mM MgCl$_2$, 1 percent NP40, 250 mM sucrose, 10 mM Tris-HCl, pH 7.5 1.5 mM hydroxystilbamidine isethionate (Merrell, Cincinnati, OH). Nuclei and membranes were cleared from the homogenate (750 xg, 5 m), and the polysomes were spun thru 0.5 M sucrose in 0.3 M NaCl, 50 mM Tris-HCl, pH 7.5, 5 mM MgCl$_2$, 1.5 mM hydroxystilbamidine isethionate onto a pad of 1.0 M sucrose in the same buffer (12,000 xg, 20 m). The polysome band was phenol extracted and ethanol precipitated, resuspended in water and clarified by centrifugation at 12,800 xg for 30 m. The resultant polysomal RNA preparations had A260/A280 ratios in the range 1.8–2.0.

Poly A(+) liver RNA was enriched for ATIII messages by centrifugation through a linear sucrose density gradient (15 percent–30 percent sucrose in 0.1 M NaCl, 12.5 mM EDTA, 10 mM Tris, pH 7.5, 0.15 percent Sarkosyl, Beckman SW50.1, 47 Krpm, 4 H, 20° C.). Aliquots of the fractionated RNA were used to direct in vitro protein synthesis in a $^{35}$S-menthionine supplemented rabbit reticulocyte lysate (BRL, Bethesda, MD). ATIII mRNA-containing fractions were identified by immunoprecipitation of in vitro synthesized protein with rabbit antihuman ATIII antiserum (Atlantic Antibodies, New Brunswick, Maine) (Kessler, 1976) and subsequent SDS gel electrophoresis (Laemmli, 1970).

Synthesis, Cloning and Screening of cDNA.

Reverse transcription reactions (containing from 0.1–5 µg RNA) were primed with the synthetic DNA fragments indicated in the text (approximately 200 ng) or oligo dT$_{(12-18)}$ (Collaborative) (approximately 1 µg). Double stranded cDNA was prepared, oligo dC-tailed, inserted into PstI cleaved G-tailed pBR322 and transformed into E. coli 294 as previously described (Lawn et al., 1981).

E. coli transformants were screened with $^{32}$P 5'-end-labeled synthetic oligonucleotides or $^{32}$P-labeled DNA prepared by random priming of given restriction fragments as previously described in Lawn et al. (1981). The synthetic DNA fragments used as primers and probes were prepared by the phosphotriester method (Crea and Horn, 1980). Procedures for DNA preparation and restriction enzyme analysis have also been published (Lawn et al., 1981).

Hybridization Selection of ATIII mRNA.

Approximately 4 µg of a 230 bp DNA fragment from plasmid pA3 was coupled to 25 mg DBM-cellulose using the procedure developed by Noyes and Stark (1975). This DNA cellulose was used to isolate ATIII-specific mRNA from 1 mg of human liver polysomal RNA utilizing the conditions described in Bock et al. (1982).

Construction of the expression plasmid.

Procedures for DNA fragment isolation and conditions for the ligation reactions have been published elsewhere (Lawn et al., 1981) and are applicable herein. Synthesis of fragments connecting the promoter and 5' end of the gene are described below.

Synthesis of Eco RI-Hind III fragment.

The principles underlying the design of the 36-base (dCTAGAATTCTATGCACGGCTCG CCAGT-GGACATCTG) and 37-base (dCGCAAGCTTCCGCGGCTTGGCTGTGCA-GAT GTCCACT) oligonucleotides used to synthesize the 45 bp EcoRI-HindIII fragment are presented in detail infra. The 36-mer and 37-mer were phosphorylated at their 5' ends with T4 polynucleotide kinase (P-L), and 2 µg of each oligonucleotide were annealed together for 10 min at 68° C., 12 m at 20° C. and 12 m at 4° C. in a volume of 40 µl. The annealing reaction was supplemented with deoxynucleotide triphosphates to 400 µM each and 5 units of E. coli DNA polymerase Klenow fragment (BRL) (total volume =50 µl). The polymerization reaction was incubated for 30 min at 20° C. and 1 h at 37° C. Buffer for the polymerization reaction contained 50 mM NaCl, 6 mM Tris.HCl, pH 7.5, 6 mM Mg Cl$_2$, 5 mM DTT, and 100 µg/ml BSA; the annealing reaction contained these same components at 1.25 X strength. After polymerization, the reaction mixture was deproteinized by phenol and chloroform extraction and digested sequentially with HindIII and EcoRI. The resultant 45 bp fragment was purified by electrophoresis in a 15 percent polyacrylamide gel.

Synthesis of 40 bp EcoRI-SacII fragment.

A 1400 bp PstI fragment containing the 5' end of the ATIII structural gene was isolated from pA62. 25 µg of this fragment and 3 µg of 5' phosphorylated 36-mer (used previously for synthesis of the EcoRI-HindIII fragment) were incubated in 33 µl H$_2$O at 100° C. for 5 m, then quick frozen. This annealing reaction was thawed and adjusted to a final volume of 50 µl containing 20 mM KCl, 8 mM MgCl$_2$, 30 mM DTT, 20 mM Tris.HCl, pH 8.3, 500 µM each dGTP, dATP, dCTP and dTTP, and 25 units reverse transcriptase (BRL). The reaction was incubated for 10 m at 20° C. and 50 m at 42° C. After deproteinization, the DNA was treated with 7 units E. coli DNA polymerase Klenow fragment (Boehringer) as described previously. Digestion with SacII and EcoRI followed Klenow treatment and produced the desired 40 bp fragment which was gel isolated.

DNA sequencing.

DNA sequence analysis was performed by the methods of Maxam and Gilbert (1980) and Sanger, Nicklen and Coulson (1977).

Protein Analysis.

Cell pellets containing 1 $A_{550}$ unit were obtained at various stages during the fermentation of antithrombin expression plasmids ATIII-E7 and pATIII-J4 (transformed into E. coli strain W3110). Each sample was resuspended in buffer containing 40mM imidazole Cl, pH 7.5, 2 percent SDS, 10 percent glycerol and 5 percent BME, and boiled for 3m. Samples were subjected to electrophoresis in the gels systems of Laemmli (1970) or Weber and Osborn (1969). Total protein was visualized by Coomassie Brilliant Blue staining and bacterially synthesized ATIII was identified by Western blot analysis (Renart et al, 1975).

Results

Initial cDNA clone for human antithrombin III.

A recombinant plasmid containing 600 bp of the ATIII structural gene was identified in a cDNA bank prepared from size fractionated RNA by hybridization to synthetic DNA fragment probes.

The published partial protein sequence of human antithrombin III (Petersen et al., 1979) was inspected for regions with limited codon degeneracy. Two such regions were identified and the corresponding synthetic DNAs of 14 or 16 nucleotides in length were prepared (Table I).

The more C-terminally located of these sequences, a pool of eight 16 mers, was used to prime cDNA synthesis from poly(A)+ RNA which had been enriched for ATIII mRNA. Previous in vitro translation studies have suggested that ATIII mRNA constitutes only 0.5 percent of bovine liver poly(A)+RNA (MacGillivray et al., 1979). We therefore enriched for ATIII encoding RNA by sucrose density gradient centrifugation, and identified the desired fraction by immunoprecipitation of ATIII from in vitro translation assays. Approximately 250 transformants were obtained upon insertion of the oligo dC-tailed, double stranded cDNA produced by specifically primed reverse transcription of the size fractionated RNA into PstI cleaved, oligo dG-tailed pBR322. Colony hybridization of this clone bank to the $^{32}P$ 5'-end-labeled 14-and 16-base synthetic nucleotides (Table I) revealed one transformant with strong hybridization to the 16mer, but not to the 14mer. DNA from this plasmid, designated pA3, was subjected to sequence analysis, and its nucleotide sequence was shown to correspond to the protein sequence of human antithrombin III extending from amino acid 239 towards the C terminus for approximately 200 residues (FIG. 1).

The identification of a clone encoding a portion of ATIII 3' to amino acid residue 243 was unexpected since the cDNA from which this clone bank was constructed had been primed with a pool of 16-base oligonucleotides predicted to encode the region around amino acid 243. Transcripts from the complementary primer were therefore expected to extend in the 5' direction from amino acid 243 and should have not included sequences 3' to the probe. In actual fact, pA3 begins near to the C-terminus of the mature protein and extends for only 12 nucleotides 5' to the probe sequence, thus hybridizing with the 16mer pools, but not the 14mers (which are located in a more N-terminal region of the protein). This particular cDNA clone perhaps resulted from the self-priming of ATIII RNA species for the reverse transcription reaction.

cDNA Clones for the Complete ATIII Structural Gene.

An internal restriction fragment from pA3 was used to purify the antithrombin III messenger RNA subsequently used for generating an oligo-dT primed cDNA clone bank. Two overlapping cDNA clones which together encode the entire human ATIII structural gene and its associated 5' and 3' untranslated regions were isolated from this bank.

DNA cellulose was prepared from the 230 bp DdeI fragment of pA3 and used to select complementary sequences from 1 mg of human polysomal liver RNA as outlined supra. In vitro translated protein from an aliquot of the bound RNA was considerably enriched for antithrombin III. The hybrid-selected RNA was used to direct oligo-dT primed cDNA synthesis. Double stranded cDNA was again cloned into the PstI site of pBR322 through homopolymeric dGC tailing, this time yielding about 500 transformants. Quadruplicate filters of the clone bank were made and screened with 4 probes distributed along the length of the ATIII structural gene (FIG. 1). The four hybridization probes were: (a) the pool of eight N-terminal 14 mers (N-14 mers) synthesized for the initial screening experiment, (b) the pool of eight 16 mers also used in the initial screening (i-16 mers), (c) a 14-base synthetic DNA (i-14mer, dTGAGGACCATGGTG) whose sequence had been determined by sequencing of pA3 and was complementary to the coding strand at amino acid 271–276 (numbering scheme as per Peterson et al., 1979), and (d) the 230 bp DdeI fragment from pA3 (which had also been used for mRNA hybridization selection).

28 of the 500 colonies generated by oligo dT priming of hybridization-selected RNA were positive when screened with the DdeI fragment used for RNA enrichment. The length of ATIII cDNAs inserted in these transformants was assessed by hybridization to the three more N-terminal probes: 20 were positive with the i-14 mer probe, 17 with the pool of 16 mers, and 3 with the

TABLE I

Synthetic DNA fragments used for cloning human antithrombin III

| Amino Acid Position* | Protein Sequence | Synthetic DNA Sequence | Use |
|---|---|---|---|
| 17 | MetAsnProMetCys | 5' dCACATAGGGTTCAT 3' (with G/A/T/C variants) | hybridization probe |
| 243 | MetMetTyrGlnGluGly | 5' dCCCTCCTGGTACATCA 3' (with T/T/A variants) | hybridization probe; cDNA primer |

*Numbering system of Petersen et al., 1979.

N-14 mers. The latter 3 plasmids had inserts of about 1.8 kb and were analyzed further. Partial DNA sequencing of these plasmids verified that they did indeed encode the amino terminus of mature human antithrombin III.

Subsequent restriction mapping and DNA sequencing of one plasmid, pA62, revealed the primary structure of an ATIII mRNA composed of an extended 5' untranslated region and a coding region of 1390 bps. pA62, however, was incomplete at the 3' end of the gene. The homopolymeric dGC tails began after the second nucleotide of the codon for the carboxyl terminal amino acid residue. Thus, this plasmid was missing the last nucleotide of the C-terminal codon, the stop codon and the 3' untranslated region.

Further analysis of partial length ATIII cDNA clones in the library constructed from oligo dT primed, hybridization-enriched mRNA revealed a plasmid, pA68, which contained 400 bps from the 3' end of the antithrombin III structural gene, an 84 bp 3' untranslated region, and a poly(A) tail. Sequence analysis of pA68 and the overlapping clone, pA62, has provided the complete primary structure of the human antithrombin III gene and portions of its flanking, untranslated regions. In addition, common restriction sites within the overlapping regions of the partial cDNA clones have been utilized to construct a full length structural gene which has been inserted into an expression plasmid so as to direct the synthesis of human antithrombin III under trp operator-promoter control in E. coli.

Sequence and Structure of the human antithrombin III messenger RNA.

Nucleotide sequence analysis of the A62 and A68 cDNA clones reveals that ATIII mRNA has a 96 nucleotide signal sequence (32 amino acids), a 1296 nucleotide sequence encoding the mature protein (432 amino acids), and 84 residues in the 3' untranslated region.

DNA sequencing reveals that a signal peptide of 32 residues probably precedes the mature N terminus of human antithrombin III. This sequence displays two features commonly attributed to signal peptide regions (Jackson and Blobel, 1980). First, a very hydrophobic region (LeuLeuSerLeuLeuLeuIle) is observed about ten residues prior to the cleavage site. Second, the presence of a cysteine immediately prior to the mature N terminus is in agreement with the precedent that the amino acid residue immediately preceding the cleavage site has in all cases been one of the smallest amino acids.

The mature form of human antithrombin III contains 432 amino acid residues. The protein sequence determined by DNA analysis agrees perfectly with the partial sequence published by Petersen et al. (1979) and has provided definitive sequence information for the regions where the original amino acid determinations were ambivalent or unknown. Amino acid residues 100, 101, 326 and 328 (numbering scheme as per Peterson) which were identified only as Glx by protein sequencing have been unambiguously determined as gln, gln, gln, and gln. Residue number 329 is an asp. DNA sequencing has also revealed that eight additional amino acids (ValLeuValAsnThrIleTyrPhe) occur between Leu 213 and Lys 214 of the sequence, which Petersen et al. (1979) did not appreciate.

Finally, the nucleotide sequence of ATIII cDNA indicates that the carboxy terminus of this protein is not processed, since the C-terminal residue of the mature protein, lysine, is immediately followed by a stop codon. The 3' noncoding region consists of 84 nucleotides following the termination codon UAA. The sequence AATAAA is present at minus 30 residues from the polyadenylation site.

Figure 3:
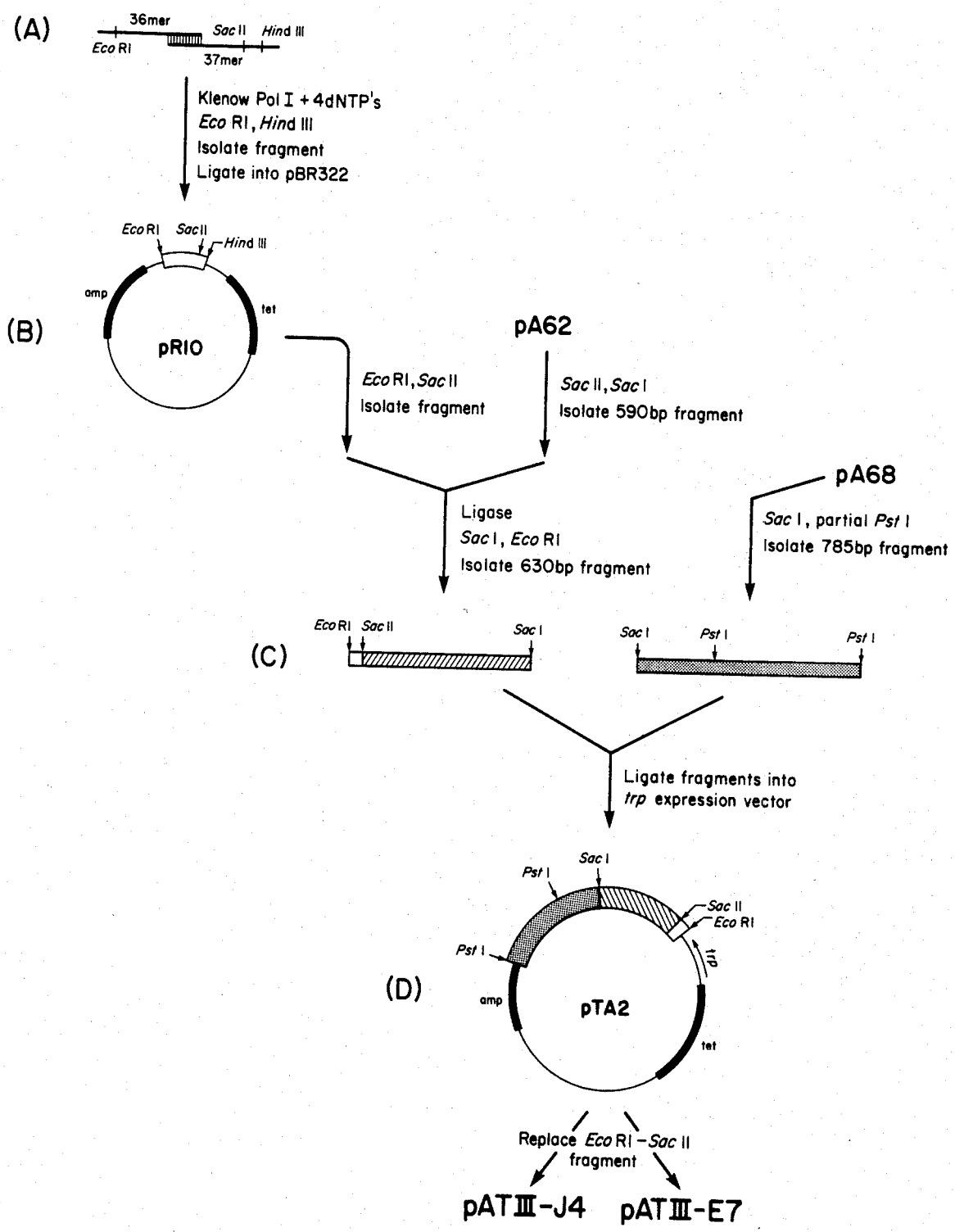
FIG. 3 depicts the construction of pATIII-E7, details of which are provided infra. (A) Synthesis of 45 bp EcoRI-HindIII fragment by DNA Pol I extension of overlapping synthetic oligonucleotides. (B) The synthetic fragment from (A), indicated by an open box, was ligated into the EcoRI-HindIII sites of pBR322, whose genes for ampicillin (amp) and tetracycline (tet) resistance are shown by dark boxes. A 40 bp EcoRI-SacI fragment was isolated from pR10 and ligated to a 590 bp fragment (shown by cross-hatched box) isolated from pA62. (C) EcoRI-SacI and SacI-PstI (dotted box) fragments were ligated into the trp expression vector fragment of LeIFA trp 103 (Gray et al., Nature 295, 503 (1982)) to yield pTA2. (D) pTA2 is a tetracycline resistant plasmid containing ATIII structural gene sequences under control of the E. coli trp operon. To correct a two nucleotide deletion found in the structural gene, the EcoRI-SacII fragment was replaced with fragments synthesized by different means. The resulting constructions, pATIII-E7 and pATIII-J4, resulted respectively in synthesis of the human mature (with accommodation of methionyl first amino acid) ATIII and human pre ATIII polypeptides in E. coli cells.

Bacterial Expression of Human Antithrombin III pATIII-E7, a 7 kb plasmid producing 50,000 dalton methionyl-ATIII, was constructed by placing segments of partial cDNA clones pA62 and pA68 behind the E. coli trp promoter (FIG. 3). Construction of this expression plasmid necessitated the synthesis of a DNA fragment incorporating an EcoRI cleavage site, an ATG translation initiation codon and the nucleotide sequence encoding the amino terminus of the mature structural gene, through the first unique restriction site, SacII. We attempted to synthesize such a fragment by a combination of chemical and enzymatic procedures. A 36 base deoxyoligonucleotide was synthesized which contained 3 arbitrarily chosen nucleotides followed by the six base EcoRI recognition sequence, then TATG and the 23 nucleotides encoding the first eight codons of mature human antithrombin III.

This synthetic 36-mer was designed to provide optimal spacing between the ribosome binding sequence and the start of translation, as well as to minimize secondary structure in the 5' end of the gene. To accomplish this, the triplets selected to encode amino acid residues 2, 3 and 4 do not correspond to the natural codons observed in the pA62 cDNA clone. A 37 base deoxyoligonucleotide which anneals to the 3' end of the 36 mer by 12 base pairs and extends towards the 3' terminus of the gene was also synthesized. Reading from its 3' to 5' end, the 37 mer contains nucleotides coding for amino acid residues 4 through 13 (containing a SacII recognition sequence) and an artificial HindIII site to be employed in propagating the linker fragment. The 36- and 37 mers were annealed, and the initial 12 bp long double stranded region was extended with DNA polymerase Klenow fragment. The duplex product was trimmed with EcoRI and HindIII and the purified EcoRI to HindIII fragment was inserted into pB322. DNA sequence analysis of the insert from this construction, pR10, revealed that the synthetic DNA was missing 2 adjacent nucleotides of the desired sequence.

The deletion may result from improper extension of this particular set of synthetic DNAs by the DNA polymerase employed. A method for correcting the 2-base deletion is discussed below. Before this was developed, the fragment containing the deletion was utilized as a convenient EcoRI to SacII linker for constructing a direct expression plasmid.

The EcoRI to SacII fragment from pR10 was used to join segments of the pA62 and pA68 partial cDNA clones to the trp promoter in pBR322. Approximately 120 ng of the EcoRI to SacII fragment from pR10 was ligated to about 1 μg of the 590 bp SacII to SacI fragment from pA62. A 630 bp EcoRI to SacI DNA fragment was gel isolated following restriction of the ligation mixture with the appropriate enzymes. This EcoRI to SacI fragment was joined to the 785 bp DNA fragment produced by SacI complete and PstI partial digestion of pA68, and a pBR322 expression vector having EcoRI and PstI ends in a three part ligation reaction. The expression vector contains a trp promoter-operator fragment which is inserted at the EcoRI site of pBR322 and reads towards the amp gene. An EcoRI sequence follows the promotor ribosome binding site; and the PstI site in the amp gene is used to fuse the vector to the 3'end of the structural gene. The product of this 3-part ligation is designated pTA2.

A derivative pTA2. was made by substituting its 38 bp EcoRI to SacII fragment with a 40 bp piece of synthetic DNA which contains an EcoRI site, initiation codon and intact coding sequence for amino acid residues 1 through 12 of ATIII. This 40 bp DNA fragment was synthesized by a process which utilized two different DNA polymerase enzymes. First, a 36 base long primer was hybridized to a template DNA fragment from pA62 and extended using the polymerase activity of AMV reverse transcriptase. (See supra. for a description of 36-mer.) Following primer elongation, the dual 3' to 5' exonuclease and 5' to 3' polymerase activities of *E. coli* Klenow fragment were exploited to trim off excess single stranded template DNA and polymerize the first several codons of the structural gene, the translation initiation codon and the EcoRI tail. The preparation was subsequently cut with EcoRI and SacII and the 40 bp fragment was inserted into pTA2. pATIII-E7, the resultant plasmid, was verified to have the correct coding information between the EcoRI and SacII sites by DNA sequence analysis. Furthermore, pATIII-E7 produces a 50,000 dalton protein under trp control which has been immunologically identified as antithrombin III.

Additionally, pATIII-Jb 4, a plasmid expressing pre-antithrombin III under trp operator-promoter control has been constructed. pATIII-J4 was derived from pTA2 by replacement of the 38 bp Eco RI - Sac II fragment with a 145 bp Eco RI - SacII fragment encoding the presumptive 36 residue signal sequence of antithrombin III and the first 12 aminoacids of the mature polypeptide. This fragment was synthesized from a 24-base synthetic DNA primer (dCTAGGAATT-CATGTATTCCAATGTG) and the 1400 bp pA62 Pst I fragment by sequential DNA polymerase I, Sac II and Eco RI treatments (Lawn et al, 1981). PATIII-J4 expresses two proteins under trp control which react with ATIII antisera. The major component has an apparent molecular weight approximating the calculated molecular weight of pre-antithrombin III. A minor band was present that comigrates with the ATIII band produced from pATIII-E7.

Inactivation of human thrombin by bacterially synthesized antithrombin III.

ATIII inactivates thrombin by reacting with it to form a covalent, 1:1 stoichiometric complex (Jesty, 1979). For example, cell extract of *E. coli* W3110 transformed with pATIII-J4 can be incubated with human thrombin in the presence of heparin. Following polyacrylamide gel electrophoresis, ATIII thrombin complexes are detected by Western blotting (Renart, et al., 1979) with rabbit anti-human ATIII antiserum. The bacterial ATIII-human thrombin complex is observed in reactions to which thrombin has been added.

Pharmaceutical Compositions

The compounds of the present invention can be formulated according to known methods to prepare pharmaceutically useful compositions, whereby the human antithrombin III product hereof is combined in admixture with a pharmaceutically acceptable carrier vehicle. Suitable vehicles and their formulation, inclusive of other human proteins, e.g. human serum albumin or plasma preparations, are described for example in *Remington's Pharmaceutical Sciences* Mark Publishing Co., Easton, Pa., 15th 2nd., 1975, which is hereby incorporated by reference. Such compositions will contain an effective amount of the protein hereof together with a suitable amount of vehicle in order to prepare pharmaceutically acceptable compositions suitable for effective administration, preferably parenteral, to the host.

Notwithstanding that reference has been made to particular preferred embodiments, it will be further understood that the present invention is not to be construed as limited to such, rather to the lawful scope of the appended claims.

Bibliography

1. Abildgaard, U. Scand. J. Haemat. 5: 440–453 (1968).
2. Abildgaard, U. et al. Scand. J. Clin. Lab. Invest. 26 (4): 349–354 (1970).
3. Bock, S. C. et al. Proc. Natl. Acad. Sci. USA 79: 1032–1036 (1982).
4. Collen, D. et al. Eur. J. Clin. Invest. 7: 27–35 (1977).
5. Crea, R. and Horn, T. Nucl. Acids Res. 8: 2331–2348 (1980).
6. Damus, P. S. et al. Nature 246: 355–357 (1973).
7. Egeberg, O. Thromb. Diath. Haemorrh. 13: 516–530 (1965).
8. Fagerhol, M. K. et al. Scand. J. Haematol 7 (1): 10–17 (1970).
9. Jackson, R. C. and Blobel, G. Annals N.Y. Acad. Sci. vol. 343 (1980).
10. Jesty, J. J. Bio. Chem. 254: 1044–1049 (1979).
11. Kessler, S. W. J. Immunology 117: 1482–1490 (1976).
12. Kurachi, K. et al. Biochemistry 15 (2): 373–377 (1976).
13. Laemmli, U. K. Nature 277: 680–685 (1970).
14. Lawn, R. M. et al. Nucl. Acids Res. 9: 6103–6114 (1981).
15. Lizardi, P. M. J. Cell. Biol. 87: 292–296 (1980).
16. Mannucci, L. et al. Scand. J. Gastroenterol. Suppl. 8 (19): 103–107 (1973).
17. Maxam, A. M. and Gilbert, W. Methods Enzymol. 65: 499–560 (1980).
18. Nordenman, B. et al. Eur. J. Biochem. 78 (1): 195–204 (1977).
19. (Noyes B. E. and Stark, G. R. Cell) 5: 301–310 (1975).
20. Odegard, O. R. et al. Scand. J. Haematol. 18: 86–90 (1977).
21. Owen, W. G. Biochimica et Biophysica Acta. 405: 380–387 (1975).
22. Petersen, T. E. et al. In *The Physiological Inhibitors of Coagulation and Fibrinolysis*. (D. Collen, B. Wiman and M. Verstraete, eds.) Elsevier, Amsterdam. p. 48 (1979).
23. Renart, J. et al. Proc. Natl. Acad. Sci. USA. 76: 3116–3120. (1979)
24. Rosenberg, R. D. et al. J. Biol. Chem. 248 (18): 6490–6505 (1973).
25. Sanger, F., Nicklen, S. and Coulson, A. R. Proc. Natl. Acad. Sci. USA 74: 5463–5467.
26. Sas, G. et al. Thrombos. Diathes. Haemorrh. (Stuttg.) 32: 105 (1979).
27. Schipper, H. G. et al. Lancet 1 (8069): 854–856 (1978).
28. Stead, N. et al. J. Biol. Chem. 251: 6481–6488.
29. Ullrich, A. et al. Science 196, 1313–1315 (1977).
30. Van der Meer, J. et al. J. Clin. Path. 26: 532–538 (1973).
31. Weber, K., and Osborn, M. J. Biol. Chem. 244: 4406–4412

We claim:

1. A DNA sequence consisting of a sequence encoding human antithrombin III.

2. The DNA sequence according to claim 1 with a sequence consisting of encoding the presequence peptide for human antithrombin III.

3. A replicable DNA cloning vehicle containing the DNA sequence according to claims 1 or 2.

4. A DNA expression vector comprising a DNA sequence encoding human antithrombin III operably linked to expression effecting DNA sequence and flanked by translational start and stop signals.

5. A viable cell culture transfected with the expression vector of claim 4.

6. A microbial cell culture of claim 5 capable of producing mature human antithrombin III.

7. Plasmids pATIII-E7 and pATIII-J4.

8. A cell culture transfected with each of the plasmids according to claim 7.

9. A culture of microbial cells transfected with a DNA expression vector encoding and capable of expressing a DNA sequence for human antithrombin III.

10. A process which comprises expressing a gene encoding human antithrombin III in a microbial cell culture transfected with a DNA expression vector operably harboring said gene.

* * * * *

UNITED STATES PATENT AND TRADEMARK OFFICE
CERTIFICATE OF CORRECTION

PATENT NO. : 4,517,294
DATED : May 14, 1985
INVENTOR(S) : SUSAN C. BOCK, RICHARD M. LAWN

It is certified that error appears in the above-identified patent and that said Letters Patent is hereby corrected as shown below:

Column 2, line 39, "$\zeta$—," should read -- $\lambda$—, --;

Column 3, line 43, "PbR322" should read --pBR322--;

Column 3, line 44, "carriers" should read --carries--;

Column 3, line 57, "EcoRi" should read --EcoRI--;

Column 5, line 6, "EcorRI-SacI" should read --EcoRI-SacI--;

Column 5, line 48, "4 H," should read --4 h,--;

Column 5, line 50, "$^{35}$S-menthionine" should read --$^{35}$S-methionine--;

Column 8, line 58 "Peterson" should read --Petersen--;

Column 9, line 44 "priro" should read --prior--;

Column 9, line 55 "Peterson" should read --Petersen--;

Column 10, line 38; "pB322." should read --pBR322.--;

Column 11, line 25, "pATIII-Jb4" should read --pATIII-J4--; and

Column 11, line 33, the DNA primer sequence "(dCTAGGAATT-" should read --(dCTAGAATT- --.

Signed and Sealed this

Twenty-third Day of September 1986

[SEAL]

Attest:

DONALD J. QUIGG

Attesting Officer

Commissioner of Patents and Trademarks